United States Patent [19]

Hickey et al.

[11] Patent Number: 5,421,972

[45] Date of Patent: Jun. 6, 1995

[54] PROCESS AND APPARATUS FOR REMOVING SOLUBLE CONTAMINANTS FROM HYDROCARBON STREAMS

[75] Inventors: Thomas P. Hickey; John J. Byeseda, both of Harris County, Tex.

[73] Assignee: National Tank Company & Catalytic Distillation Technologies, Pasadena, Tex.

[21] Appl. No.: 263,264

[22] Filed: Jun. 21, 1994

Related U.S. Application Data

[63] Continuation of Ser. No. 963,571, Oct. 19, 1992, abandoned.

[51] Int. Cl.⁶ .............................................. B01D 17/06
[52] U.S. Cl. ..................................... 204/186; 204/188; 204/305
[58] Field of Search .............. 204/186, 188, 189, 190, 204/191, 302, 305

[56] References Cited

U.S. PATENT DOCUMENTS

| | | | |
|---|---|---|---|
| 4,606,801 | 8/1986 | Prestridge et al. | 204/186 |
| 4,702,815 | 10/1987 | Prestridge et al. | 204/302 |
| 4,804,453 | 2/1989 | Sublette et al. | 204/302 |
| 5,022,973 | 6/1991 | Thornton | 204/186 |

OTHER PUBLICATIONS

J. D. Thornton, The Application of Electrical Energy to Chemical and Physical Rate Processes, Rev. Pure and Appl. Chem, vol. 18, pp. 197, 212-218 (1968).

P. J. Balles, Solvent Extraction in an Electrostatic Field, Ind. Eng. Chem. Process Des. Dev., 1981, No. 20, pp. 564-570.

*Primary Examiner*—John Niebling
*Assistant Examiner*—William T. Leader
*Attorney, Agent, or Firm*—Kenneth H. Johnson

[57] ABSTRACT

A method for removing soluble contaminants, such as acetonitrile, from a non-polar hydrocarbon stream into a polar water stream by countercurrent flow between an electrostatic field generated by a pair of parallel electrodes. The electrostatic field is modulated in strength to produce a dispersing, mixing, coalescing, and settling cycle that is effective to mix and separate the fluids.

4 Claims, 2 Drawing Sheets

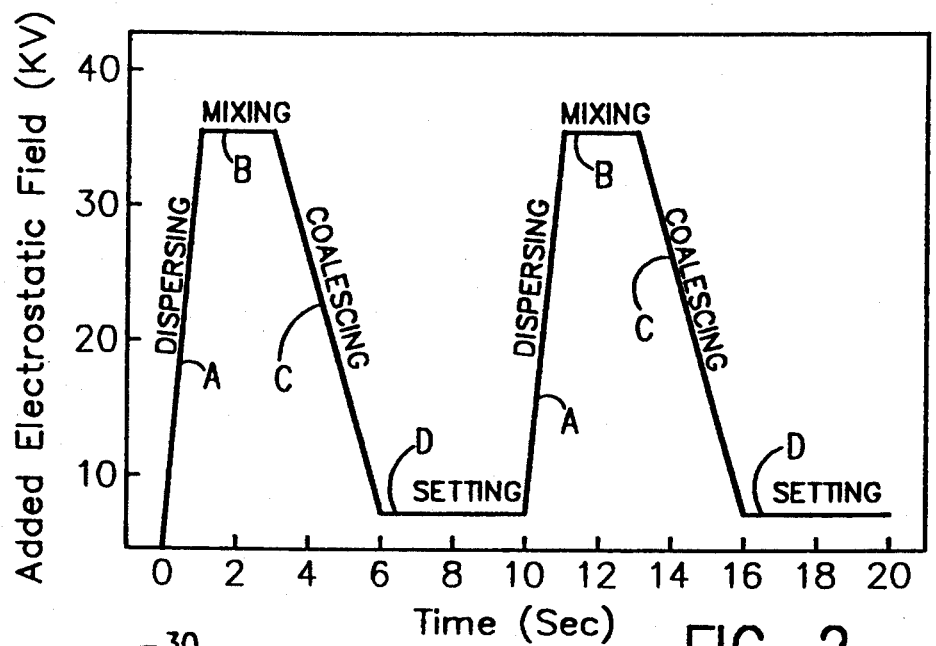
FIG. 2
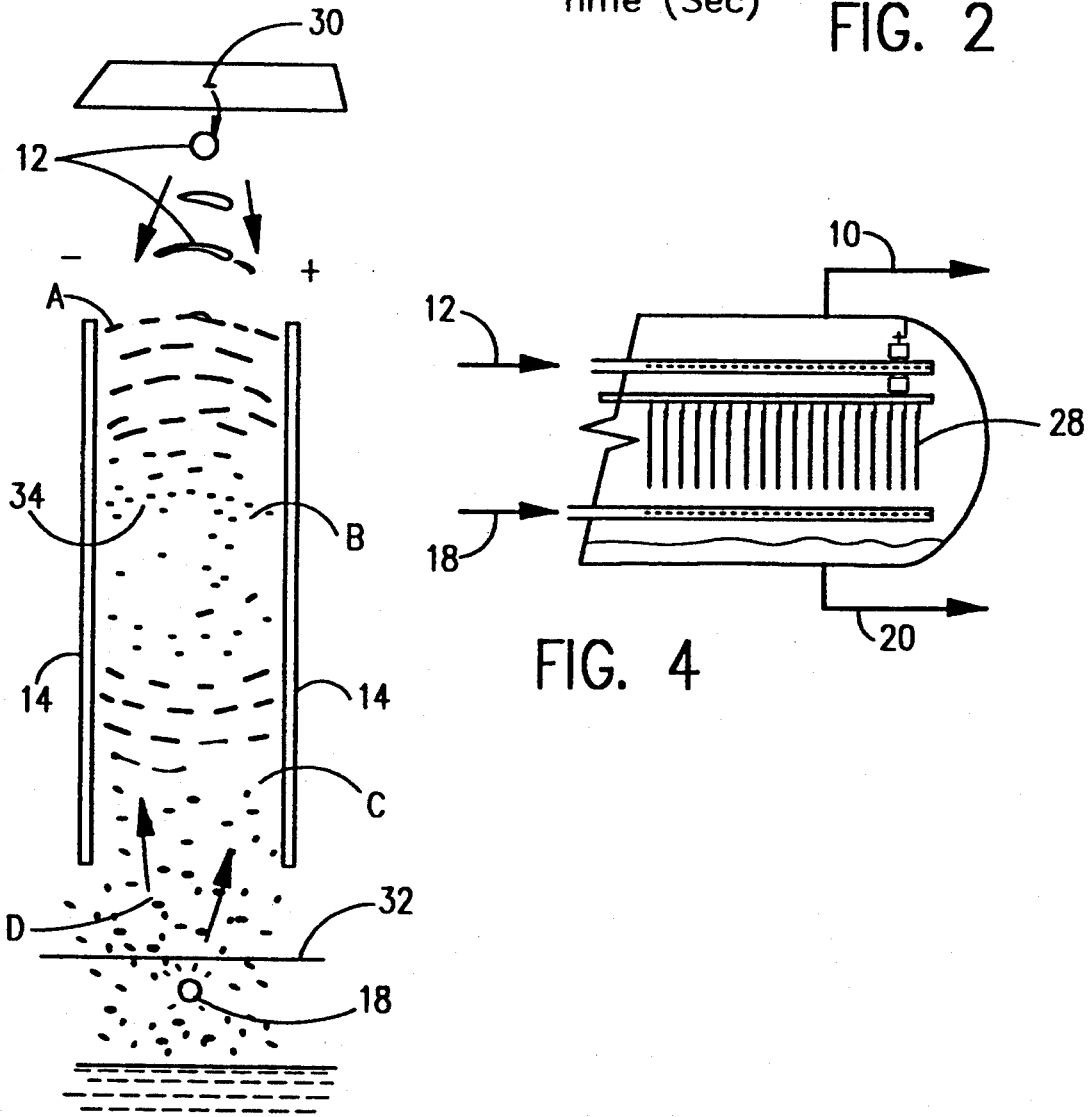
FIG. 3
FIG. 4

PROCESS AND APPARATUS FOR REMOVING SOLUBLE CONTAMINANTS FROM HYDROCARBON STREAMS

This application is a continuation of application Ser. No. 07/963,571, filed Oct. 19, 1992, now abandoned.

BACKGROUND OF THE INVENTION

1. Field of the Invention

This invention relates to electrostatic separation process and apparatus for the removal of acetonitrile from $C_4$ and $C_5$ hydrocarbon streams by passing a stream of water in counterflow to the direction of flow of the hydrocarbon through an electric field of varying electric field gradient established by a plurality of composite electrodes.

2. Description of the Prior Art

The Clean Air Act Amendments of 1990 have forced refiners to search for ways to introduce oxygen into gasoline to produce cleaner burning reformulated fuels. The leading component to satisfy these needs is Methyl Tertiary Butyl Ether (MTBE). MTBE has a high blending octane number and relatively low vapor pressure and is an excellent blending component. Other ethers presently to enter this market are tertiary amyl methyl ether (TAME) and ethyl tertiary butyl ether (ETBE).

MTBE is formed by the reaction of isobutylene and methanol at mild operating conditions (100°–180° F., 100 psig) over a catalyst. The high selectivity of the reaction at these conditions allows 94–95% of the reactive hydrocarbon to be converted to MTBE as limited by equilibrium constraints. By using a catalytic distillation column, essentially complete conversion is attainable. TAME and ETBE are formed in comparable processes by the reaction of isoamylene with methanol and the reaction of isobutylene with methanol, respectively.

The etherification processes utilize strongly acidic ion exchange resins as etherification catalysts. These are strongly acidic organic polymers. As an isobutylene or isoamylene molecule meets alcohol at an active site, the reaction takes place rapidly forming ether.

The activity of the catalyst for the etherification reaction is a function of the acid loading or capacity of the resin. This functionality is not linear; a loss of 20% of acid sites on the catalyst gives approximately 50% loss of activity for conversion to MTBE. It is therefore important to minimize the deactivation of the catalyst with effective feed pretreatment to maintain peak performance and long catalyst life.

The loss of catalytic activity may be caused by the adsorption of basic compounds or metal ions, the blockage of the active sites by polymeric products, or by the splitting off of the functional groups due to long term operation at temperatures above 240° F. The latter two causes are affected by the operating conditions of the MTBE unit. The major source of lost activity is typically from poisons entering with the feedstocks to the unit. Poisons to the catalyst include basic compounds such as ammonia, amines, caustic soda, and acetonitrile (ACN).

In refinery applications, the largest source of hydrocarbon feedstock containing isobutylene is the $C_4$ stream from the cat cracking unit (FCCU). Some $C_4$'s are also obtained from fluid or delayed cokers. ACN is formed in these units that enters the etherification process with the hydrocarbon feed stream. The amount of ACN in the feed varies with the severity of the cat cracker operation, crude source, and catalyst used in the FCCU. The ACN level of refinery based MTBE unit feeds may range from <10 ppm to >550 ppm. Unlike all the other feed poisons which deactivate the catalyst in a plug flow fashion through the catalyst bed, ACN's deactivation mechanism is not immediate and results in a diffused deactivation throughout the entire bed. Catalyst deactivation by ACN occurs through the catalyzed hydrolysis of ACN to acetic acid and ammonia and the subsequent neutralization of the acid sites by the ammonia.

In order to obtain adequate run lengths with the catalyst and optimum performance, the first step in the etherification process is a feed pretreatment step designed to remove the poisons to very low levels (<1 ppm). Since the poisons are much more soluble in water than hydrocarbon, the common treatment is a multistage water wash. The water and hydrocarbon streams are contacted utilizing trays or packing. In the tower the continuous water phase flows down the column as the liquid hydrocarbon droplets are dispersed upwards. Of the many poisons to the catalyst, ACN is the most troublesome. The tower design is based on ACN removal to 1 ppm. The design variables include the number of theoretical contact stages and the flow rate of water. In most typical refinery MTBE units, a minimum of three contacting stages and at relative flow rate of 30 weight percent water to hydrocarbon is required to reduce ACN levels to the 1 ppm specification. This results in a tower containing at least three beds of at least 8 feet of packing in each bed, or 12–16 trays. The column must also contain sufficient height to allow the less dense hydrocarbon phase to separate from the water phase. This is important as free water can have an adverse effect on the catalyst.

The amount of wash water required is also an important design variable. Wash water flow at 20 weight percent of the hydrocarbon is a minimum amount based on the efficiency of the liquid-liquid contacting. In many cases, much higher rates are used. This in turn results in a large flow of waste water extract leaving the column which must be handled either by reusing it in other refinery processes or more commonly, discharging it to the effluent treating plant.

In summary, an important part of any refinery based etherification process is feed pretreatment to remove catalyst poisons so that economical catalyst life and high ether production rates are achieved. Early MTBE plants have water wash systems designed before the importance of ACN removal was recognized. Inadequate removal of ACN in those units gave catalyst bed life as short as six months. Water wash systems designed to effectively remove ACN has demonstrated catalyst life from 12 to 24 months. Optimization of this step to make it more efficient resulting in reduced capital investment, operating expense, and water usage is extremely attractive.

A liquid-liquid extraction process has three steps:
1. Intimate contact between the two phases
2. Coalescence of dispersed phase drops
3. Separation of the phases Conventional liquid-liquid extraction devices use mechanical energy to create drops. The rate of mass transfer is proportional to the interfacial area, so one strives to create dispersed phase drops as small as practical. If the drop size is too small, residence time required for phase separation makes the contactor too large and too costly. Conventional phase contact devices generally use minimum dispersed phase drop diameters of approximately 0.5-1.0 millimeter.

Extraction processes are often used when distillation is difficult or ineffective. Extraction utilizes differences in the solubilities of the components rather than differences in their volatilites. Extraction takes advantages of chemical differences between components rather than vapor pressure differences as in distillation.

In liquid-liquid extraction two phases must be brought into good contact to permit transfer of material and then be separated. In extraction, since the two phases have comparable densities, the energy available for mixing and separation is small. The two phases are often hard to mix and harder to separate. The viscosities of both phases, also, are relatively high, and linear velocities through most extraction equipment are low. Therefore, in some types of extractors, energy for mixing and separation is supplied mechanically. This requires additional expense in equipment, maintenance, and operating costs.

U.S. Pat. No. 4,702,815 discloses a system for removing brine from oil well production. A fresh water or less saline water is passed in counterflow to the oil well production through electric fields established by composite electrodes.

U.S. Pat. No. 4,804,553 discloses a countercurrent dilution water flow system coupled with the electrostatic mixing of the dilution water with the brine inherent in oil well production. A plurality of parallel conductive electrode plates in which the voltage applied to the electrode plates is modulated becoming the equivalent of a multi-stage mixer/coalescer/separator.

U.S. Pat. No. 4,606,801 discloses a method and apparatus for dispersing or mixing relatively polar fluids in a relatively non-polar fluid. The fluids are passed between electrostatic fields that are modulated to effectively mix and separate these fluids.

The present invention is an improvement over conventional extraction techniques. It is an advantage that conventional type mixing and separation equipment are not needed. Generally, the electrostatic separation systems have been applied to the removal of connate insolubles in oil streams and other solid/liquid dispersions, no procedure has addressed the removal of hydrocarbon soluble materials into water by liquid-liquid extraction.

SUMMARY OF THE INVENTION

Broadly the present method of soluble contaminant removal comprises electrostatically separating a contaminant soluble in a non-polar liquid stream from said non-polar liquid stream into a polar liquid stream, the polarity of said streams being relative between said streams, comprising the steps of:

(a) first flowing the non-polar stream between at least a pair of electrodes, (b) flowing the polar stream between the pair of electrodes, the streams preferably flowing countercurrent, (c) applying a voltage to the electrodes to establish an electrostatic field having the strength to shear and disperse the polar liquid into the non-polar liquid, (d) maintaining a strength of the electrostatic field to accomplish mixing the polar liquid with the non-polar liquid in order to extract the contaminant from the non-polar liquid into the polar liquid, (e) reducing the voltage applied to the electrodes to coalesce the dispersed polar liquid, (f) maintaining a low voltage on the electrodes for a predetermined period to allow coalesced droplets of polar liquid to settle and separate from the non-polar liquid.

More preferably present invention relates to a method for removing acrylonitrile impurities from a $C_4$-$C_5$ hydrocarbon stream by an electrostatic extraction and the apparatus for carrying out the method.

Briefly a fresh water or less acrylonitrile contaminated stream is passed counterflow to the $C_4$-$C_5$ hydrocarbon stream through electric fields established by electrodes. The power to the electrostatic field is modulated for the purpose of first mixing and then separating immiscible fluids in the electrostatic field. The acrylonitrile impurities are removed from the hydrocarbon stream by extraction into the water phase, without a dilution effect on the hydrocarbon stream. This extraction process differs significantly from the electrostatic methods used to dilute brine in oil well production.

The apparatus of the present invention is that described for carrying out the process.

BRIEF DESCRIPTION OF THE DRAWINGS

FIG. 2 is a graph of the variation of the applied voltage to the electrodes with time.

FIG. 3 shows the internal operation of the electrostatic separator in FIG. 1.

FIG. 4 shows a multistage electrostatic separator arrangement.

DESCRIPTION OF THE PREFERRED EMBODIMENTS

Figure 1:
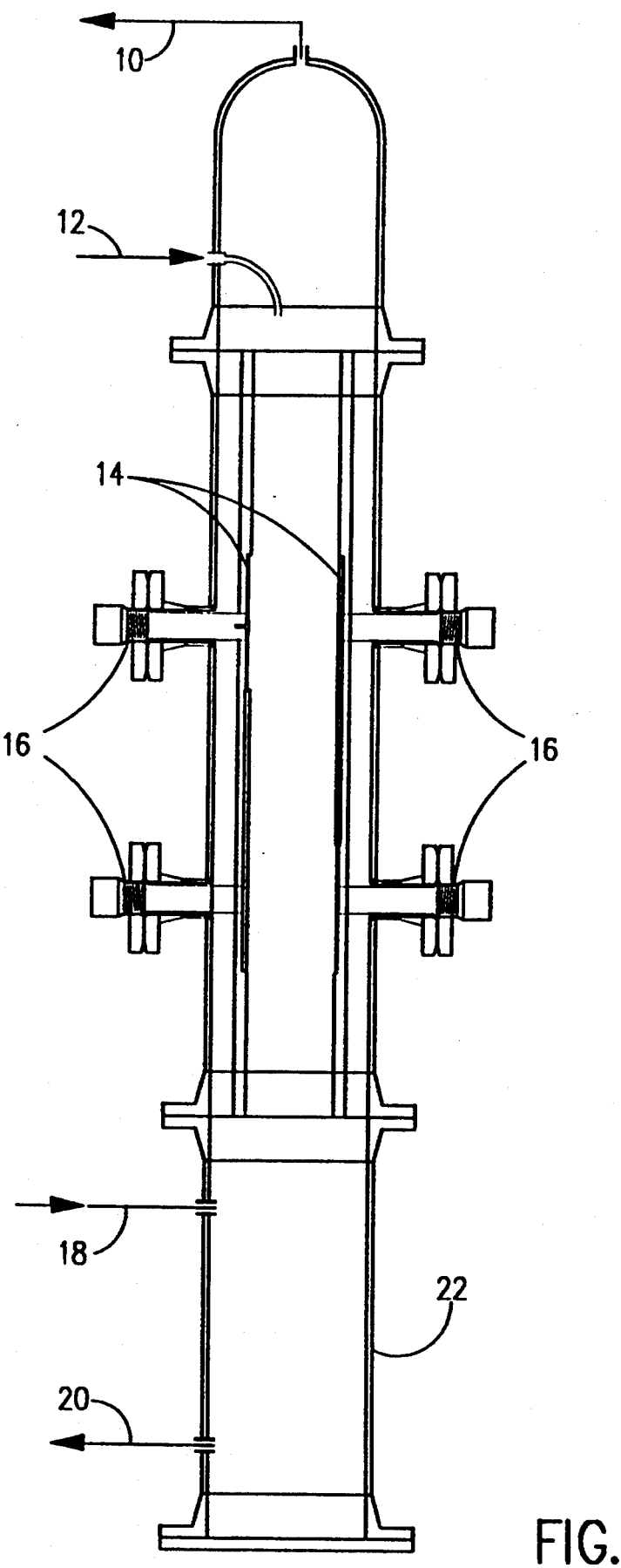
FIG. 1 shows the electrostatic separator.

Electrostatic phase contacting and separation can create much smaller dispersed phase droplets (0.01-0.05 millimeter) while maintaining the ability to separate phases in a relatively compact package.

After creating interfacial area for mass transfer, dispersed phase drops must coalesce before separation. Coalescence occurs in two steps. First the drops must coagulate: a surface-chemical process that reduces forces stabilizing the dispersion such that drops can approach close enough for the attractive force between droplets to overcome electrostatic repulsion.

Flocculation is the prelude to coalescence. First the drops collide. If the drops are properly coagulated, they stick together as a flocculated aggregate. This aggregate may coalesce into a single larger droplet provided there are no physical barriers (suspended solids, surfactant films) bound at the droplet interface.

Flocculation can be promoted chemically, although adding chemicals to a closed loop process may cause problems. Flocculation by electric fields is preferred if the continuous phase is non-conductive relative to the dispersed phase. Electroflocculation has been commercially applied for several decades for water washing crude petroleum for salt removal.

Phase separation in a solvent extraction process relies upon retention time in a quiescent zone to allow the flocculated drops to settle. The droplet size dominates behavior of a solvent extraction process since the drops must be large enough for practical phase disengagement.

Direct current (DC) fields for flocculation have several beneficial effects. The dispersed water drops experience the attraction in a steady, unidirectional field so that the attractive force causes droplets to move toward each other. Therefore, coalescence effects dependent on drop proximity are enhanced. Migration ultimately results in movement of drops to one of the charged electrodes where they acquire a net charge from the electrode. In an array of oppositely charged electrodes, the charged drops then immediately accelerated toward the oppositely charged electrode. This results in drops of opposite charge flowing in opposite directions. The net result is a large increase in flocculation between droplets.

Corrosion is a potential problem in any metal/electrolyte system in the presence of an electrical current. In an AC system, the rapid directional change in the current reverses the electrolytic reactions before diffusion of the reaction products makes these reactions irreversible. In a DC system, the electrolytic reactions are continuous, and corrosion can be a serious problem.

The benefits of both AC and DC fields can be obtained by an electrical arrangement that places a DC field across adjacent electrodes while maintaining an AC field between these electrodes and electrical ground. The containment vessel and the water layer are at ground potential, so that corrosion is virtually eliminated. And AC field induced coalescence at the oil/water interface is maintained. Between the electrodes, DC induced migration of water droplets and enhanced electroflocculation result in greater droplet growth and better performance than an AC field.

An equilibrium drop size is reached in an electroflocculation device that depends on field strength, with smaller drops occurring at higher field strength. Small drops require a high electric field gradient to achieve significant coalescence. Thus the field strength necessary to reduce the remnant water content of an organic stream to low levels (<0.1 wt %) may produce a small equilibrium drop size that produces problems for phase separation.

There are two approaches for avoiding this compromise. One approach varies the field strength as a function of time, and the other is to vary the electric field strength as a function of position in creating space. In the first, the field strength is subjected to a periodic variation that coalesces small droplets in a strong field, and then allows further drop growth in a declining field. FIG. 2 illustrates the concept of field strength variation as a function of time. Since the drops are settling as this occurs, the small droplets that settle slowly are subjected to repeated cycles while large drops fall out of the affected zone during periods of low field strength.

The field strength can also be varied along its vertical axis by using resistive electrodes to generate the field. Again, the larger drops migrate downward into the zone of lower field strength which results in further growth. In practice, both methods may be applied simultaneously.

Just as declining field strength can enhance drop growth, increasing field strength can decrease drop size by electrostatic mixing. Drop diameters of 1-5 microns can be produced by electrostatic mixing. Several mechanisms contribute to this effect:

(a) Increasing migration velocity at high field strength leads to increased hydrodynamic shear resulting in drop deformation and division.

(b) If the field strength oscillates near the resonant frequency of the drops, oscillations resulting in drop shatter are produced.

(c) Drop charge of sufficient magnitude has been shown to produce instability leading to drop shattering.

It should be noted in each of these mechanisms that the forces leading to dispersion are largely confined to the dispersed phase with minimum power used to accelerate the continuous phase. Conventional extraction devices spend most of the power on accelerating the continuous phase.

The rate of mass transfer in an extraction process is proportional to the interfacial area. Generally, one would like to operate with the smallest dispersed phase droplet size to obtain the highest mass transfer rate consistent with the intrinsic reaction rate of any chemical reaction. For a conventional extraction process that uses mechanical energy to mix phases, the dispersed droplet size is limited by the gravity phase separation process incorporated in the equipment. Since electrostatic energy can be used to control dispersed droplet size, one can build a countercurrent extractor that allows mass transfer to occur when the drops are small and disengages phases when the drops are larger.

FIG. 1 shows the electrostatic separator having a pair of electrodes 14 that are supported by high voltage bushings 16 disposed within a vessel 22. The contaminant is contained within the continuous (non-polar) phase 18 and enters the vessel 22 flowing up through the modulated electrostatic field generated between electrodes 14. The electrostatic field is modulated to effect a dispersing A, mixing B, coalescing C, and settling D sequence shown in FIG. 2. Although vertical flow for the contaminated fluid is preferred, the invention is not limited to this configuration, as the contaminated fluid may be flowed in any direction to enter the electrostatic field. At the same time the continuous phase 18 is introduced, the dispersed (polar) phase 12 is introduced, flowing downward through the electrodes 14.

FIG. 3 shows a detailed view of the electrostatic separation process between the electrodes 14. The continuous (non-polar) phase 18 and enters from the continuous phase header 32 flowing up through the modulated electrostatic field generated between electrodes 14. At the same time the dispersed phase 12 enters from the dispersed phase header 30 and proceeds downward into the electrostatic field, which is modulated to first shear the polar fluid into small droplets and disperse them into the relatively non-polar fluid where they are mixed with the contaminant. These dispersed droplets then contact and unite with the contaminant in the non-polar fluid and are coalesced into droplets large enough to gravitate through the electrostatic field between the electrodes. This sequence is repeated many times as the fluid moves through the electrostatic field, allowing the polar fluid to gravitate downward and producing numerous countercurrent mixing stages. FIG. 2 shows a graph of the dispersing A, mixing B, coalescing C, and settling cycle D that is repeated as the fluid moves through the electrodes.

FIG. 4 shows an alternative embodiment of a multistage electrostatic separator (ELECTRODYNAMIC™ Contactor). The dispersed phase 12 enters the vessel through a header placed above the electrode array 28 if this phase has higher density than the other phase. The continuous phase enters below the electrodes. The continuous phase 18 must be a relatively non-conductive organic phase to maintain the electrostatic field.

As the electrostatic field is modulated as shown on FIG. 2, the dispersed phase 12 shatters to fine droplets (10-50 micron) for efficient mass transfer during the dispersing and mixing part of the cycle. During the coalescing and settling part of the cycle, the dispersed phase drops grow large enough to settle in the continuous phase to a slightly lower position in the electrode array before the next mixing and dispersing cycle begins. Thus many mixing and coalescing cycles occur while the dispersed phase is held between the electrodes. Many theoretical stages of extraction can be obtained in a single pass through the electrodes.

EXAMPLE 1

This work was done using a pilot vessel as shown in FIG. 1, constructed as a single channel (4"×4") to simulate the exact geometry of a full scale commercial unit. The electrode length used for pilot work was 24". Commercial units can be built with up to 6' long electrodes. The pilot configuration has been proven to correlate with operation of full scale electrostatic contacting systems for other applications. TABLE I illustrates some typical results. The $C_4$ feedstock obtained from a commercial MTBE plant.

TABLE I

| Flow | | In $C_4$ | Out $C_4$ | | |
|---|---|---|---|---|---|
| $C_4$ lb/hr | Water lb/hr | ACN ppm | ACN ppm | Water/ $C_4$ (%) | Stages (Kd = 7) |
| 120 | 13 | 49 | 18 | 11 | 3 |
| 100 | 13 | 24 | 6 | 13 | 4 |
| 90 | 15 | 42 | 4 | 17 | 5 |
| 144 | 13 | 40 | 3 | 9 | 8 |
| 80 | 15 | 13 | 1 | 19 | 6 |

The pilot operating data shows that for a range of typical operating conditions, the electrostatic contactor operates with 6" or less for one theoretical stage of contact. This contrasts with a typical packed tower or sieve tray contactor for this application which operates with HETP in the range of 6 to 8 feet.

EXAMPLE 2

Table II illustrates the performance for a commercial scale apparatus of the present process washing the $C_4$ feed to an MTBE Unit. The results are based on a distribution coefficient $K_d=7$ (mass concentration of ACN in water/ACN in $C_4$ phase). The contactor design is based on electrode length to give 10 equilibrium stages.

TABLE II

| Feed $C_4$ ACN (wppm) | Wash Water as mass % of $C_4$ | Outlet $C_4$ ACN (wppm) |
|---|---|---|
| 100 | 25 | 0.2 |
| 100 | 20 | 1.0 |
| 100 | 15 | 7.0 |
| 50 | 25 | 0.1 |
| 50 | 20 | 0.5 |
| 50 | 15 | 3.5 |
| 25 | 25 | 0.1 |
| 25 | 20 | 0.3 |
| 25 | 15 | 1.8 |

A conventional feed pretreatment tower designed for 13000 BPD at 20% or 30% wash water rate requires a relatively tall vertical tower. The present process requires a horizontal vessel much shorter than the height of the conventional tower. Additionally, the water consumption could be reduced to 15 mass % or less. The savings in total installed cost for the new process can be up to 40% of the total installed cost for a conventional system. Reducing ACN levels to 1 ppm or less can increase both the catalyst life and MTBE production.

The invention claimed is:

1. A method for electrostatically removing acetonitrile from a $C_4$-$C_5$ stream into a water stream comprising the steps of:
   (a) flowing the water stream between at least a pair of electrodes in a vessel,
   (b) concurrently flowing the $C_4$-$C_5$ stream containing acetonitrile between the pair of electrodes countercurrent to said water stream in said vessel,
   c) applying a voltage to the electrodes to establish an electrostatic field having the strength to shear and disperse the water into the $C_4$-$C_5$ stream,
   (d) maintaining a strength of the electrostatic field to accomplish mixing the water fluid with the $C_4$-$C_5$ stream, to extract a portion of said acetonitrile into said water,
   (e) reducing the voltage applied to the electrodes to coalesce the dispersed water,
   (f) maintaining a low voltage on the electrodes for a predetermined period to allow coalesced droplets of said water to settle and separate from the $C_4$-$C_5$ stream;
   (g) removing the water containing the acetonitrile from one end of said vessel; and
   (h) removing the $C_4$-$C_5$ stream having a reduced acetonitrile content from the opposite end of said vessel.

2. The method according to claim 1 wherein said flowing is substantially horizontal.

3. A method for electrostatically separating a contaminant comprising acetonitrile and soluble in a non-polar liquid stream comprising $C_4$ hydrocarbons from said non-polar liquid stream into a polar liquid stream comprising water, the polarity of said streams being relative between said streams, comprising the steps of:
   (a) flowing the non-polar stream comprising $C_4$ hydrocarbons containing a contaminant comprising acetonitrile dissolved therein between at least a pair of electrodes,
   (b) flowing the polar stream between the pair of electrodes,
   (c) applying a voltage to the electrodes to establish an electrostatic field having the strength to shear and disperse the polar liquid into the non-polar liquid,
   (d) maintaining a strength of the electrostatic field to accomplish mixing the polar liquid with the non-polar liquid in order to extract the contaminant from the non-polar liquid into the polar liquid,
   (e) reducing the voltage applied to the electrodes to coalesce the dispersed polar liquid,
   (f) maintaining a low voltage on the electrodes for a predetermined period to allow coalesced droplets of polar liquid to settle and separate from the non-polar liquid.

4. A method for electrostatically separating a contaminant comprising acetonitrile and soluble in a non-polar liquid stream comprising $C_5$ hydrocarbons from said non-polar liquid stream into a polar liquid stream comprising water, the polarity of said streams being relative between said streams, comprising the steps of:
   (a) flowing the non-polar stream comprising $C_5$ hydrocarbons containing a contaminant comprising acetonitrile dissolved therein between at least a pair of electrodes,
   (b) flowing the polar stream between the pair of electrodes, (c) applying a voltage to the electrodes to establish an electrostatic field having the strength to shear and disperse the polar liquid into the non-polar liquid, (d) maintaining a strength of the electrostatic field to accomplish mixing the polar liquid with the non-polar liquid in order to extract the contaminant from the non-polar liquid into the polar liquid, (e) reducing the voltage applied to the electrodes to coalesce the dispersed polar liquid, (f) maintaining a low voltage on the electrodes for a predetermined period to allow coalesced droplets of polar liquid to settle and separate from the non-polar liquid.

* * * * *